United States Patent
Shikata et al.

(10) Patent No.: US 10,080,551 B2
(45) Date of Patent: Sep. 25, 2018

(54) STOOL COLLECTION CONTAINER (71) Applicant: SHIMADZU CORPORATION, Kyoto-shi, Kyoto (JP)

(72) Inventors: Masamitsu Shikata, Kyoto (JP); Naoko Takaoka, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 84 days.

(21) Appl. No.: 15/405,446

(22) Filed: Jan. 13, 2017

(65) Prior Publication Data

US 2018/0199922 A1 Jul. 19, 2018

(51) Int. Cl.
- *A61B 10/00* (2006.01)
- *B01L 3/00* (2006.01)
- *G01N 1/08* (2006.01)

(52) U.S. Cl.
CPC ...... *A61B 10/0038* (2013.01); *B01L 3/50825* (2013.01); *G01N 1/08* (2013.01); *B01L 2200/025* (2013.01); *B01L 2300/042* (2013.01)

(58) Field of Classification Search
CPC ............ A61B 10/0038; A61B 10/0096; B01L 3/50825; G01N 1/08
See application file for complete search history.

(56) References Cited

U.S. PATENT DOCUMENTS

| | | | | |
|---|---|---|---|---|
| 5,149,506 A * | 9/1992 | Skiba | ................ | A61B 10/0038 209/17 |
| 5,514,341 A * | 5/1996 | Urata | ................ | A61B 10/0038 422/534 |
| 7,908,935 B2 * | 3/2011 | Hasegawa | .......... | A61B 10/0038 73/864.44 |
| 9,149,258 B2 * | 10/2015 | Wan | .................. | A61B 10/0038 |
| 9,211,112 B2 * | 12/2015 | Lidgard | ............. | A61B 10/0038 |
| 2015/0182202 A1 * | 7/2015 | Wan | ...................... | B01L 3/5023 600/562 |
| 2017/0224315 A1 * | 8/2017 | Bastia | ................ | A61B 10/0038 |

FOREIGN PATENT DOCUMENTS

JP 2009-276311 A 11/2009

* cited by examiner

*Primary Examiner* — Justin Olamit
(74) *Attorney, Agent, or Firm* — Sughrue Mion, PLLC (57) ABSTRACT

A stool collection container includes: a stool collection container main body having a structure in which a stick holder for holding a stool collection stick is detachably mounted on one end side while the stool collection part and the stool collection stick are housed inside; and a collection needle penetrating through a wall surface of the another end side of the stool collection container main body so that a tip thereof is inserted into the stool collection container main body, the collection needle being provided so as to be detachable from the stool collection container main body. When the stick holder is mounted on one end side of the stool collection container main body, the tip of the collection needle is inserted into the opening of the stool collection part housed inside the stool collection container main body.

16 Claims, 6 Drawing Sheets

FIG. 6 ial Field

The present invention relates to a stool collection container for collecting and storing stool to be used for stool examinations.

BACKGROUND ART

When testing for the presence of bacterial capable of causing food poisoning such as *Escherichia coli, Bacillus dysentericus*, or *Salmonella*, a method called cultivation is typically used. Cultivation entails spreading a portion of collected stool over an agar medium, cultivating the sample, and testing for the presence or absence of bacterial colony formation so as to assess whether target bacteria are contained in the stool.

Ordinarily, stool serving as a specimen is collected using a special stick at the home of each individual undergoing the test, and the entire stick is housed in a prescribed container (for example, see Patent Literature 1). The stick for collecting stool has a shape that facilitates the collection of stool and facilitates application to an agar medium. Because it is necessary to keep the bacteria contained in the collected stool alive, a gel-like medium is provided inside the container housing the stick.

In recent years, testing for bacteria capable of causing food poisoning is transitioning to genetic testing methods using PCR technology instead of cultivation. Examinations based on stool tests are performed for the purpose of not only establishing a definite diagnosis of infections but also rapidly screening uninfected people.

Some testing organizations that perform screening process over 10,000 specimens per day. When screening large numbers of specimens, a method of collecting a plurality (for example, 50) of specimens and simultaneously performing PCR reaction processing while taking advantage of the characteristics of PCR, which enables highly sensitive detection, so as to reduce the number of PCR reaction processes and to perform rapid detection is used. When a positive specimen emerges, the specimen is retested by cultivation in order to confirm whether the bacteria are alive.

PRIOR ART LITERATURE

Patent Literature (Patent literature 1) Japanese Unexamined Patent Application Publication 2009-276311

SUMMARY OF THE INVENTION

Problem to be Solved by the Invention

At a testing organization that perform stool tests, the following process is performed: a stick with stool adhered to the tip is removed from the container, and a portion of the stool adhered to the tip of the stick is collected with a toothpick or the like and added to a specimen treatment liquid. At the time of this process, it is necessary for the operator conducting the test to transfer the container and the toothpick from one hand to the other after removing the stick from the container. When processing many samples, this process becomes complex, and it takes a long time to process all of the samples. In addition, it also becomes important for the tool such as a toothpick used to collect stool from the stick to be free of contamination, so the management of the tool becomes necessary.

Therefore, an object of the present invention is to provide a stool collection container with which a portion of stool collected on the tip of a stick for a stool test can be easily collected.

Means for Solving the Problem

The stool collection container of the present invention comprises: a stool collection part having an opening for holding stool; a stool collection stick for holding the stool collection part at a tip thereof so that the opening is aligned with a front tip part; a stick holder for holding a base end of the stool collection stick; a stool collection container main body having a space inside for housing the stool collection part and the stool collection stick, having an insertion slot for inserting the stool collection stick from the tip side on one end side, and having a structure for detachably mounting the stick holder on one end side while the stool collection part and the stool collection stick are housed inside; and a collection needle penetrating through a wall surface of the another end side of the stool collection container main body so that a tip thereof is inserted into the stool collection container main body, the collection needle being provided so as to be detachable from the stool collection container main body; the tip of the collection needle being inserted into the opening of the stool collection part housed inside the stool collection container main body when the stick holder is mounted on one end side of the stool collection container main body.

A medium for preventing the extermination of bacteria present in stool is preferably provided at a position inside the stool collection container main body where the stool collection part is disposed when the stick holder is mounted on one end side of the stool collection container main body. As a result of a medium being provided inside the stool collection container main body, it is possible to store bacteria present in collected stool without exterminating the bacteria.

In a preferred mode, the stool collection container further comprises a separation part which holds a base end of the collection needle and is provided at the other end of the stool collection container main body in a state wherein the separation part can be detached together with the collection needle from the stool collection container main body by a manual operation. As a result, an operator can easily remove the collection needle from the stool collection container main body, which enhances the specimen collection efficiency.

The stool collection container preferably further comprises a sealing member for sealing a through-hole through which the collection needle passes, the through-hole being provided in the wall surface of the other end side of the stool collection container main body, after the collection needle is detached from the stool collection container main body. As a result, it is possible to prevent the drying of stool inside the stool collection container main body, the leakage of the medium provided inside the stool collection container main body, or the like after the collection needle is removed.

One example of the sealing member is a cap mounted on the other end side of the stool collection container main body.

In a preferred mode in the case described above, a portion of the stool collection container main body where the cap is mounted has a cylindrical shape, and threads which screw into threads provided on the inner peripheral surface of the gap are provided on the outer peripheral surface thereof so that the cap may be mounted on the other end of the stool collection container main body by rotating the cap.

Effect of the Invention

The stool collection container of the present invention comprises: a stool collection container main body having a structure in which a stick holder for holding a stool collection stick is detachably mounted on one end side while the stool collection part and the stool collection stick are housed inside; and a collection needle penetrating through a wall surface of the another end side of the stool collection container main body so that a tip thereof is inserted into the stool collection container main body, the collection needle being provided so as to be detachable from the stool collection container main body; the tip of the collection needle being inserted into the opening of the stool collection part housed inside the stool collection container main body when the stick holder is mounted on one end side of the stool collection container main body. Therefore, by simply mounting the stick holder on one end of the stool collection container main body after stool is collected in the stool collection part, the tip of the collection needle is inserted into the opening of the stool collection part at the tip of the stool collection stick so as to come into contact with the collected stool. Accordingly, a portion of the stool can be collected from the stool collection part at the tip of the stick holder by simply detaching the collection needle from the stool collection container main body, so the specimen collection operation is easy.

MODE FOR CARRYING OUT THE INVENTION

Figure 1:
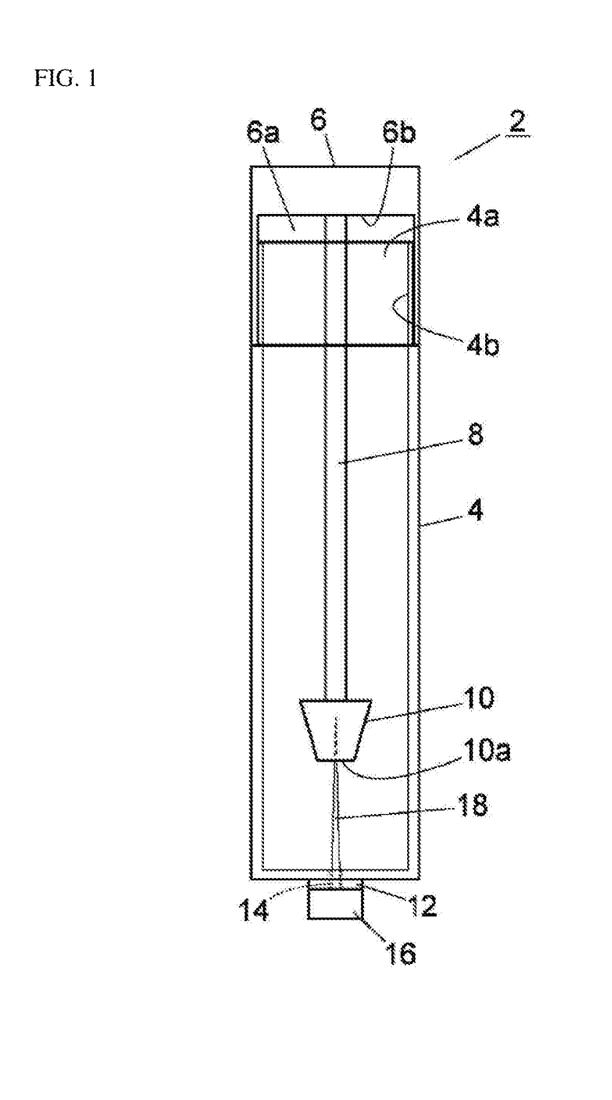
FIG. 1 is a front view illustrating a working example of the stool collection container.
Figure 2:
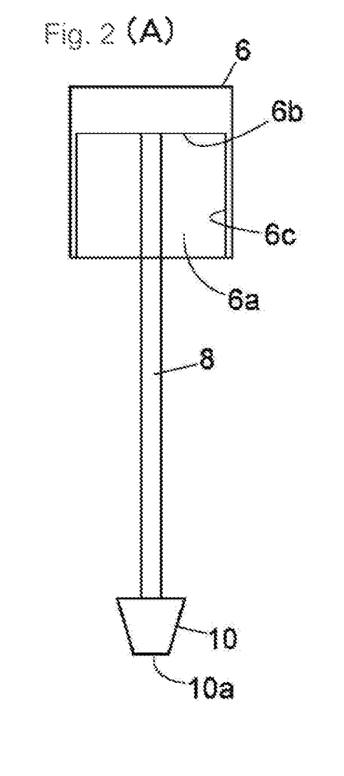
FIGS. 2(A) and 2(B) illustrates a state in which the stool collection stick has been removed from the stool collection container main body of this working example, wherein (A) is the stool collection stick that has been removed from the stool collection container main body, and (B) is the stool collection container main body.
Figure 3:
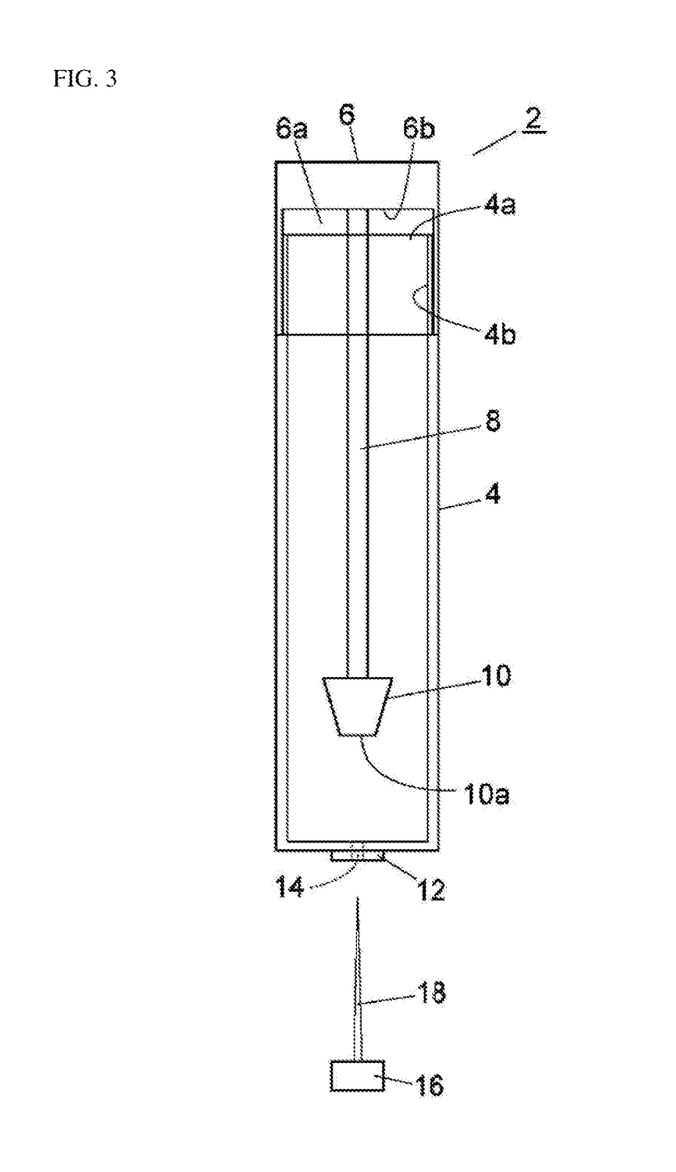
FIG. 3 illustrates a state in which the collection needle has been removed from the stool collection container main body of this working example.

A working example of a stool collection container will be described using FIGS. 1 to 3. In FIGS. 1 to 3, the stool collection container is drawn in a perspective state so that the internal structure can be understood.

Figure 6:
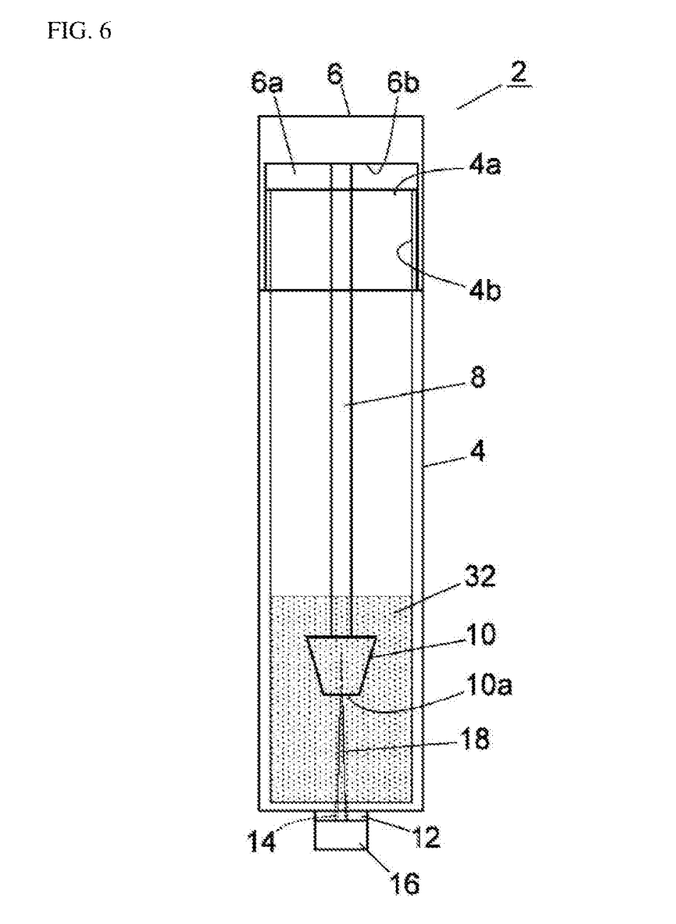
FIG. 6 is a front view illustrating a state in which a medium is provided inside the stool collection container main body of this working example.

This stool collection container 2 comprises: a stool collection container main body 4 having a base, a stick holder 6 which closes an opening on one end side of the stool collection container main body 4, a stool collection stick 8 attached to the stick holder 6, and a collection needle 18 provided on the other end side of the stool collection container main body 4. Stool is collected using the stool collection stick 8, and the collected stool is housed and stored in the stool collection container main body 4 with the entire stool collection stick 8. In FIG. 1, an illustration of a medium is omitted in order to facilitate an understanding of the structure of this stool collection container 2, but as illustrated in FIG. 6, a medium 32 is provided inside the stool collection container main body 4 to enable storage while preventing the extermination of bacteria in the stool collected by the stool collection stick 8.

The stool collection stick 8 is a rod-shaped member, and a stool collection part 10 for collecting stool is provided on the tip thereof. An opening 10a for holding stool is provided at the tip of the stool collection part 10, and stool is collected in the opening 10a by thrusting the tip of the stool collection part 10 into the stool. The base end of the stool collection stick 8 is held on the stick holder 6, and the stick holder 6 and the stool collection stick 8 are formed integrally.

Figure 4:
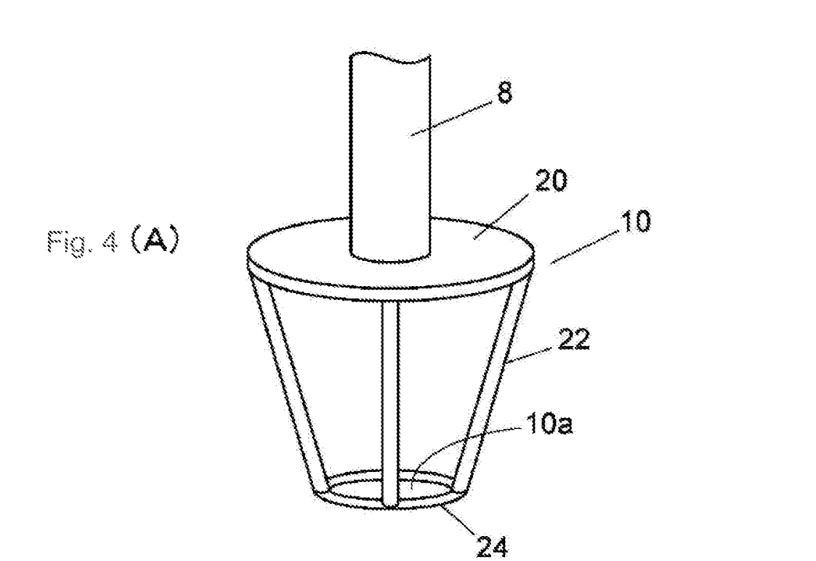
FIGS. 4(A) and 4(B) illustrates an example of the stool collection part at the tip of the stool collection stick of this working example.

The stool collection part 10 provided at the tip of the stool collection stick 8 may have any shape as long as the shape has an opening 10a with which stool can be collected and held. For example, in the example illustrated in FIG. 4(A), a disc 20 is fixed to the top of the stool collection stick 8, and a ring 24 having an outside diameter that is smaller than that of the disc 20 is attached by a frame 22 to the tip side of the disc 20. The inside of the ring 24 forms an opening 10a, and stool is held in the space enclosed by the frame 22 and the ring 24. In addition, in the example illustrated in FIG. 4 (B), a recession 28 is provided in the end face of a member 26 having a shape in which the outside diameter decreases toward the tip end, and stool is collected and held by the opening 10a of the recession 28.

Returning to FIGS. 1 to 3, the stick holder 6 has a recession 6a for housing one end part of the stool collection container main body 4 so that an insertion slot 4a of the stool collection container 4 can be sealed by covering one end part 4a (end part on the upper side in FIGS. 1 to 3) of the stool collection container main body 4 described below. The base end of the stool collection stick 8 is fixed to the bottom face 6b of the recession 6a of the stick holder 6 so that the stool collection stick 8 is housed inside the stool collection container main body 4 when the stick holder 6 is mounted on one end of the stool collection container main body 4.

The stool collection container main body 4 is a roughly cylindrical container, for example, having an insertion slot 4a for inserting the stool collection stick 8 on one end side and having another end side which is closed. The one end side 4b of the stool collection container main body 4 has roughly the same shape as the inner peripheral surface 6c of the recession 6a of the stick holder 6, and this one end part 4b is fitted into the recession 6a of the stick holder 6 so that the stool collection container main body 4 and the stick holder 6 are united. The shape of the stool collection container main body 4 is not limited to a cylindrical shape, and any shape such as a rectangular cylindrical shape may be used as long as the shape forms a container with which the insertion slot 4a on one end side can be sealed by the stick holder 6 and with which the stool collection stick 8 can be thereby housed.

Note that the structure enabling the unification of the stool collection container main body 4 and the stick holder 6 is not limited to the structure described above. For example, threads which engage with one another may be provided on one end side of the stool collection container main body 4 and the stick holder 6 side, and the threads may be screwed together so as to enable the unification of the stool collection container main body 4 and the stick holder 6.

A protrusion 12 is provided in the center of the surface on the other end side (lower side in FIGS. 1 to 3) of the stool collection container main body 4, and a separation part 16 is provided on the tip of the protrusion 12. The separation part 16 holds the collection needle 18 on a surface on the side opposite the protrusion 12. The tip part of the collection needle 18 is inserted into the stool collection container main body 4 via a through-hole 14 provided so as to pass through the protrusion 12 and the wall surface on the other end side of the stool collection container main body 4. The through-hole 14 is a circular hole, the inside diameter of which is larger than the thickness of the collection needle 18. The collection needle 18 reaches the stool collection part 10 at the tip of the stool collection stick 8 extending into the stool collection container main body 4 from the stick holder 6 mounted on one end of the stool collection container main body 4, and the tip of the collection needle 18 comes into contact with stool held in the opening 10a of the stool collection part 10.

Figure 5:
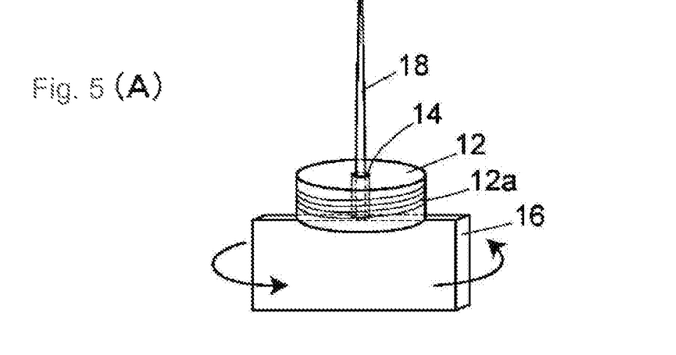
FIGS. 5(A), 5(B) and 5(C) are drawings for explaining the structure for removing the collection needle from the stool collection container main body of this working example.

The separation part 16 is fixed to the protrusion or is configured so that, as illustrated in FIGS. 5(A) and (B), for example, the separation part 16 can be easily detached from the stool collection container main body 4 by a manual operation by twisting or the like with respect to the stool collection container main body 4. The protrusion 12 remains on the stool collection container main body 4 side even after the separation part 16 is detached. In the example of FIGS. 5(A) and 5(B), the separation part 16 has a flat plate shape, but any shape such as a spherical shape, for example, may be used as long as the shape allows an operator to perform operations easily by holding and twisting the unit.

Because the collection needle 18 is formed integrally with the separation part 16, the collection needle 18 can be extracted from the stool collection container main body 4 by detaching the separation part 16 from the protrusion 12. Inside the stool collection container main body 4, the tip of the collection needle 18 is in contact with stool held in the opening of the stool collection part 10, so a portion of the stool collected by the stool collection stick 8 can be easily collected by simply detaching the separation part 16 from the protrusion 12 so as to extract the collection needle 18 from the stool collection container main body 4.

The through-hole 14 provided in the wall surface on the other end side of the stool collection container main body 4 is preferably sealed after the collection needle 18 is extracted in order to prevent the drying of stool or the leakage of the medium inside the stool collection container main body 4. In the example of FIGS. 5(A)-(C), a method of providing threads on the outer peripheral surface of the protrusion 12 and sealing the through-hole 14 after the collection needle 18 is extracted with a cap 30 provided with threads which screw into the aforementioned threads on the inside surface 30a thereof is used. Another method is to wrap a self-welding film such as a plastic paraffin film, for example, around the junction portion of the protrusion part 12 and the separation part 16 so that the self-welding film automatically seals the through-hole 14 when the separation part 16 is twisted off of the protrusion part 12.

Note that it is not absolutely necessary for the protrusion part 12 to be provided, and the separation part 16 may also be provided directly on the other end surface of the stool collection container main body 4.

EXPLANATION OF REFERENCES 2 stool collection container
4 stool collection container main body
4a insertion slot
4b one end part of stool collection container main body
stick holder
6a recession
6b recession bottom surface
6c recession inner peripheral surface
8 stool collection stick
10 stool collection part
10a opening
12 protrusion
12a protrusion outer peripheral surface
14 through-hole
16 separation part
18 collection needle
30 cap
30a cap inner peripheral surface
32 medium

What is claimed:

1. A stool collection container comprising:
   a stool collection part having an opening for holding stool;
   a stool collection stick for holding the stool collection part at a tip of the stool collection stick so that the opening is aligned with a front tip part;
   a stick holder for holding a base end of the stool collection stick;
   a stool collection container main body having a space inside for housing the stool collection part and the stool collection stick, having an insertion slot for inserting the stool collection stick from a tip side on one end side, and having a structure for detachably mounting the stick holder on the one end side while the stool collection part and the stool collection stick are housed inside; and
   a collection needle penetrating through a wall surface of an other end side of the stool collection container main body so that a tip of the collection needle is inserted into the stool collection container main body, the collection needle being provided so as to be detachable from the stool collection container main body;
   the tip of the collection needle being inserted into the opening of the stool collection part housed inside the stool collection container main body when the stick holder is mounted on one end side of the stool collection container main body.

2. The stool collection container according to claim 1, wherein a medium for preventing the extermination of bacteria present in stool is provided at a position inside the stool collection container main body where the stool collection part is disposed when the stick holder is mounted on the one end side of the stool collection container main body.

3. The stool collection container according to claim 1, wherein the stool collection container further comprises a separation part which holds a base end of the collection needle and is provided at the other end of the stool collection container main body in a state wherein the separation part can be detached together with the collection needle from the stool collection container main body by a manual operation.

4. The stool collection container according to claim 2, wherein the stool collection container further comprises a separation part which holds a base end of the collection needle and is provided at the other end of the stool collection container main body in a state wherein the separation part can be detached together with the collection needle from the stool collection container main body by a manual operation.

5. A stool collection kit, comprising:
the stool collection container according to claim 1, and a sealing member for sealing a through-hole through which the collection needle passes, the through-hole being provided in the wall surface of the other end side of the stool collection container main body, after the collection needle is detached from the stool collection container main body.

6. A stool collection kit, comprising:
the stool collection container according to claim 2, and a sealing member for sealing a through-hole through which the collection needle passes, the through-hole being provided in the wall surface of the other end side of the stool collection container main body, after the collection needle is detached from the stool collection container main body.

7. A stool collection kit, comprising:
the stool collection container according to claim 3, and a sealing member for sealing a through-hole through which the collection needle passes, the through-hole being provided in the wall surface of the other end side of the stool collection container main body, after the collection needle is detached from the stool collection container main body.

8. A stool collection kit, comprising:
the stool collection container according to claim 4, and a sealing member for sealing a through-hole through which the collection needle passes, the through-hole being provided in the wall surface of the other end side of the stool collection container main body, after the collection needle is detached from the stool collection container main body.

9. The stool collection kit according to claim 5, wherein the sealing member is a cap mounted on the other end side of the stool collection container main body.

10. The stool collection kit according to claim 6, wherein the sealing member is a cap mounted on the other end side of the stool collection container main body.

11. The stool collection kit according to claim 7, wherein the sealing member is a cap mounted on the other end side of the stool collection container main body.

12. The stool collection kit according to claim 8, wherein the sealing member is a cap mounted on the other end side of the stool collection container main body.

13. The stool collection kit according to claim 9, wherein a portion of the stool collection container main body where the cap is mounted has a cylindrical shape, and threads which screw into threads provided on the inner peripheral surface of the gap are provided on the outer peripheral surface of the portion so that the cap may be mounted on the other end of the stool collection container main body by rotating the cap.

14. The stool collection kit according to claim 10, wherein a portion of the stool collection container main body where the cap is mounted has a cylindrical shape, and threads which screw into threads provided on the inner peripheral surface of the gap are provided on the outer peripheral surface of the portion so that the cap may be mounted on the other end of the stool collection container main body by rotating the cap.

15. The stool collection kit according to claim 11, wherein a portion of the stool collection container main body where the cap is mounted has a cylindrical shape, and threads which screw into threads provided on the inner peripheral surface of the gap are provided on the outer peripheral surface of the portion so that the cap may be mounted on the other end of the stool collection container main body by rotating the cap.

16. The stool collection kit according to claim 12, wherein a portion of the stool collection container main body where the cap is mounted has a cylindrical shape, and threads which screw into threads provided on the inner peripheral surface of the gap are provided on the outer peripheral surface of the portion so that the cap may be mounted on the other end of the stool collection container main body by rotating the cap.

\* \* \* \* \*